US006924381B2

(12) United States Patent
Dawson

(10) Patent No.: US 6,924,381 B2
(45) Date of Patent: Aug. 2, 2005

(54) MODIFIED PHYSICAL REFINING OF SOYBEAN OIL

(75) Inventor: Robert B Dawson, Warsaw, NC (US)

(73) Assignee: Carolina Soy Products, LLC, Warsaw, NC (US)

( * ) Notice: Subject to any disclaimer, the term of this patent is extended or adjusted under 35 U.S.C. 154(b) by 28 days.

(21) Appl. No.: 10/746,669

(22) Filed: Dec. 24, 2003

(65) Prior Publication Data

US 2005/0143590 A1 Jun. 30, 2005

(51) Int. Cl.[7] .................................................. C07C 1/00

(52) U.S. Cl. ............................ 554/12; 554/9; 426/489; 426/492; 426/634

(58) Field of Search ...................... 554/17, 9; 426/492, 426/489, 634

(56) References Cited

*Primary Examiner*—Deborah D. Carr

(74) *Attorney, Agent, or Firm*—MacCord Mason PLLC

(57) ABSTRACT

A solvent extraction free, process for producing refined soybean oil that is high in calcium and/or magnesium is described in which mechanically extracted crude soybean oil is subjected to a two-stage process to separate hydratable and nonhydratable phospholipids. In the first stage, the crude oil is intimately mixed with water or with a weakly acidic aqueous solution, e.g., a aqueous solution of citric acid or a similar organic acid, to form gums of the hydratable phospholipids. After removing the gums from the oil, e.g., by centrifuging, the oil from the first degumming is intimately mixed with a weakly basic solution, e.g., an aqueous solution of sodium hydroxide or sodium metasilicate, to produce soapstock and reduce the magnesium and calcium in the oil to less than 100 ppm, followed by separation of the soapstock, e.g., by centrifuging. Free fatty acids are then removed through physical refining.

17 Claims, No Drawings

MODIFIED PHYSICAL REFINING OF SOYBEAN OIL

BACKGROUND OF THE INVENTION (1) Field of the Invention

The present invention relates generally to a process for extracting and refining soybean oil and to the resultant product, and in particular to an improved method of separating soybean oil that is high in calcium and/or magnesium, permitting physical refining of the oil.

(2) Description of the Prior Art

Soybean oil production involves several steps that are necessary to render the soybean oil suitable for human consumption. These production steps may be broadly characterized as 1) soybean preparation, 2) oil extraction, and 3) oil refining. Soybean preparation generally includes the steps of cleaning, drying, cracking, and dehulling.

The great majority of commercial soybean oil production processes extract or separate the oil from the soybean meal by a process known as solvent extraction. In the solvent extraction process, the prepared beans are first flaked to provide a large surface area. A solvent, commonly hexane, is then pumped through the soybean flakes to dissolve the oil in the hexane, separating approximately 99.5% of the oil from the meal. The hexane is then separated from the oil and recycled.

The crude oil resulting from the solvent extraction must then be subjected to additional treatments, collectively called "refining", to remove various materials in order for the oil to be suitable for consumption. These materials include hydratable and non-hydratable phospholipids, free fatty acids, and various color and flavor components. Crude soybean oil contains phosphorous compounds called hydratable phospholipids, and small amounts of calcium and magnesium that complex with a portion of the phospholipids to form non-hydratable phospholipids. Hydratable phospholipids are normally removed by a process known as "degumming", in which the oil is agitated or otherwise intimately combined with water to precipitate gums from the oil. The gums are then removed by centrifuging.

These precipitated gums can be used as a feed additive, or evaporated to remove moisture. The end product, lecithin, has various end uses such as food emulsifier. The degummed oil is dried under vacuum to remove any water. Removal of non-hydratable phospholipids is considerably more difficult and expensive, requiring further chemical treatment, typically chemical refining, to break the chemical bonds between the calcium or magnesium ions and the phospholipids, followed with extensive bleaching of the oil.

In most processes, free fatty acids are removed from the oil by a process known as caustic refining, also called chemical or alkali refining, in which the oil is mixed with a caustic material, such as sodium or potassium hydroxide, which undergoes a saponification reaction with the acids, forming soaps that are then removed by centrifugation. Non-hydratable phospholipids are removed along with the free fatty acids. Chemical refining soybean oil is an expensive process, requiring a large investment in capital equipment. In addition, a significant quantity of the oil is captured by the soaps, adversely affecting oil yield. Also, the caustic refining process produces soapstock, which has little commercial value, and it is difficult to dispose of without environmental problems.

Conventional refining processes also involve some bleaching of the soybean oil to remove color pigments that adversely affect the color of the oil. Finally, chemicals that add flavors to the oil are removed by a process known as "deodorization", which is essentially a form of physical distilling, in which the oil is subjected to high temperatures under a vacuum for a short period of time, which is sufficient to remove the flavor-causing components, but insufficient to break down non-hydratable phospholipids.

Commonly assigned U.S. Pat. No. 6,511,690, issued Jan. 28, 2003, and copending U.S. patent application Ser. No. 10/066,250, filed Jan. 31, 2002, both the patent and application being incorporated herein by reference in their entirety, describe an alternative process for producing soybean oil having a commercially acceptable frylife, i.e., at least 30 fry cycles, without partial hydrogenation by a combination of mechanical oil extraction combined with physical refining of the crude oil. In the process described therein, soybean oil is mechanically separated from prepared soybeans by first rapidly heating the beans for up to about 60 seconds to a temperature of from about 300° F. to about 370° F., preferably from about 315° F. to about 335° F., followed by mechanically pressing the oil from the beans. Desirably, the beans are crushed during or after heating to assist in freeing the oil, e.g., by extruding the beans through an extruder in which the beans are subjected to high pressures that crush the beans while frictionally heating the beans.

The crude soybean oil is then degummed by intimately mixing the crude soybean oil with water, which may contain citric acid or a similar organic acid, to form gums of the hydratable phospholipids, which are then removed from the crude oil, e.g., by centrifuging. The degummed oil is then bleached with bleaching materials, such as clay or silica gel. The oil is then vacuum dried and filtered.

The resultant oil is a useful product known as refined and bleached oil. Normally, however the oil is further processed to remove free fatty acids and components that contribute to the color and flavor of the oil. Free fatty acids are then removed along with undesirable flavor and color components by physical refining, in which the oil is heated in a distillation column to from about 450° F. to about 500° F. to distill off the free fatty acids and flavor materials.

While the combination of mechanical extraction with physical refining results in several improvements over the solvent extraction and caustic refining process, use of physical refining is not possible for soybean oil containing a high amount of magnesium and calcium salts, i.e., more that 100 ppm. Therefore, further improvements are still needed in order to permit refining of soybean oils that are unusually high in calcium and magnesium.

SUMMARY OF THE INVENTION

Generally, the present process comprises a modification of the above-described mechanical extraction/physical refining process, and in particular comprises a two-stage removal of phospholipids from the oil, especially when the soybean oil is unusually high in calcium and/or magnesium, that may be in the form of nonhydratable phospholipids or other calcium or magnesium salts.

More specifically, soybean oil extracted from soybeans by heating and crushing the soybeans under the conditions described above, followed by pressing the crushed soybeans to separate the oil from the soybean meal, is subjected to a two-stage treatment process. The two-stage process includes the steps of 1) intimately mixing the crude oil with water or with a weakly acidic aqueous solution, e.g., a aqueous solution of citric acid or a similar organic acid, to form gums of the hydratable phospholipids, and then removing the gums from the oil, e.g., by centrifuging, and then 2) intimately mixing the oil from the degumming treatment with a weakly basic solution, e.g., an aqueous solution of an alkali metal hydroxide or metasilicate, e.g., sodium hydroxide or sodium metasilicate, to produce from soapstock of the calcium and magnesium salts, followed by separation of the soapstock, e.g., by centrifuging. To render the oil suitable for physical refining, the content of calcium and magnesium salts should be reduced to less than 100 ppm.

Overall, the soybean oil refining process of the present invention comprises the steps of:

a) heating soybeans to a temperature of at least 300° F. in less than 60 seconds;
b) crushing the soybeans to form a mixture of soybean meal and crude soybean oil;
c) separating the crude soybean oil from the soybean meal;
d) mixing the crude soybean oil with water or a weakly acidic solution to form gums of hydratable phospholipids;
e) separating the gums from the first soybean oil;
f) intimately mixing the oil from the degummed treatment with a weakly basic aqueous solution to react with the calcium and magnesium ions to produce soapstock;
g) separating the soapstock from the soybean oil;
h) bleaching the soybean oil; and
i) heating the soybean oil under a vacuum to remove free fatty acids.

DETAILED DESCRIPTION OF THE INVENTION

By way of example, cleaned and dehulled soybeans were extruded through an extruder having a 15-inch conduit, with the dwell time within the conduit being about 30 seconds. During extrusion, the beans were mechanically crushed and frictionally heated to a temperature of 315° F. to 335° F. Crushed soybeans exiting the extruder were then pressed to separate most of the oil from the soybean meal. The separated oil was screened to remove remaining solids prior to the refining process.

The crude soybean oil was then degummed with water containing citric acid and centrifuged to remove gums of the hydratable phospholipids. The resulting first degummed oil was then intimately mixing with a dilute sodium hydroxide aqueous solution to react with the calcium and magnesium salts to form soapstock, followed by separation of the soapstock by centrifuging. Sufficient sodium hydroxide is used to reduce the amount of calcium and magnesium salts to below about 100 ppm. The resultant soybean oil was then bleached, vacuum dried and filtered. The oil was then physically refined by heating the oil in a distillation column to a temperature of from about 460° F. to about 480° F., to distill off the free fatty acids and flavor materials.

Thus, the present invention provides a solvent extraction free, process for producing refined soybean oil that is high in calcium and/or magnesium is described in which mechanically extracted crude soybean oil is subjected to a two-stage process to separate hydratable and nonhydratable phospholipids. In the first stage, the crude oil is intimately mixed with water or with a weakly acidic aqueous solution, e.g., a aqueous solution of citric acid or a similar organic acid, to form gums of the hydratable phospholipids. After removing the gums from the oil, e.g., by centrifuging, the oil from the first degumming is intimately mixed with a weakly basic solution, e.g., an aqueous solution of sodium hydroxide or sodium metasilicate, to produce soapstock and reduce the magnesium and calcium in the oil to less than 100 ppm, followed by separation of the soapstock, e.g., by centrifuging. Free fatty acids are then removed through physical refining.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A process for treating crude soybean oil containing calcium and magnesium obtained from soybeans by mechanical extraction comprising:

a) mixing the crude soybean oil with water or an acidic aqueous solution to form gums of hydratable phospholipids;
b) separating the gums from the crude oil to obtain first treated soybean oil;
c) intimately mixing the first treated oil with a basic aqueous solution to produce soapstock containing calcium and magnesium, whereby the amount of calcium and magnesium remaining in the oil is less than 100 ppm; and
d) separating the soapstock from the first treated soybean oil.

2. The process of claim 1, wherein said acidic aqueous solution is comprised of water containing an organic acid.

3. The process of claim 1, wherein said basic aqueous solution is comprised of water containing an alkali metal hydroxide or an alkali metal metasilicate.

4. The process of claim 1, wherein said acidic aqueous solution is an aqueous solution of acetic acid.

5. The process of claim 1, wherein said basic aqueous solution is an aqueous solution of sodium hydroxide or sodium metasilicate.

6. A process for producing soybean oil from soybeans that are high in magnesium and calcium comprising:

a) heating said soybeans to at least 300° F.;
b) mechanically pressing said soybeans to separate soybean oil from soybean meal;
c) mixing the crude soybean oil with water or an acidic aqueous solution to form gums of hydratable phospholipids;
d) separating the gums from the crude oil to obtain first treated soybean oil;
e) intimately mixing the first treated oil with a basic aqueous solution to produce soapstock containing calcium and magnesium salts, whereby the amount of calcium and magnesium remaining in the oil is less than 100 ppm;
f) separating the soapstock from the first treated soybean oil; and
g) heating said soybean oil to a temperature of from about 450° F. to about 500° F. under a vacuum to remove free fatty acids from said soybean oil.

7. The process of claim 6, wherein said soybeans are heated to at least 300° F. in less than about 60 seconds.

8. The process of claim 6, wherein said soybeans are crushed while being frictionally heated to a temperature of from about 300° F. to about 370° F.

9. The process of claim 6, further including bleaching said soybean oil following pressing.

10. The process of claim 6, wherein said soybean oil is heated under a vacuum at a temperature of from about 460° F. to about 480° F.

11. The process of claim 6, wherein said acidic aqueous solution is comprised of water containing an organic acid.

12. The process of claim 6, wherein said basic aqueous solution is comprised of water containing an alkali metal hydroxide or an alkali metal metasilicate.

13. The process of claim 6, wherein said acidic aqueous solution is an aqueous solution of acetic acid.

14. The process of claim 6, wherein said basic aqueous solution is an aqueous solution of sodium hydroxide or sodium metasilicate.

15. A process for producing soybean oil from soybeans that are high in magnesium and calcium comprising:

a) crushing said soybeans while frictionally heating said soybeans to a temperature of from about 300° F. to about 370° F.;

b) mechanically pressing the crushed soybeans to separate crude soybean oil from soybean meal;

c) mixing the crude soybean oil with acetic acid aqueous solution to form gums of hydratable phospholipids;

d) separating the gums from the crude oil to obtain first treated soybean oil;

e) intimately mixing the first treated oil with an aqueous solution of sodium hydroxide to produce soapstock containing calcium and magnesium, whereby the amount of calcium and magnesium remaining in the oil is less than 100 ppm;

f) separating the soapstock from the soybean oil; and g) heating said soybean oil to a temperature of from about 450° F. to about 500° F. under a vacuum to remove free fatty acids from said soybean oil.

16. The process of claim 15, wherein said soybeans are heated to at least 300° F. in less than about 60 seconds.

17. The process of claim 15, further including bleaching said soybean oil following pressing.

* * * * *